(12) United States Patent
Levy (10) Patent No.: US 11,490,795 B2
(45) Date of Patent: *Nov. 8, 2022

(54) DYNAMIC FIELD OF VIEW ENDOSCOPE

(71) Applicant: 270 SURGICAL LTD, Netanya (IL)

(72) Inventor: Avraham Levy, Kfar Shmaryahu (IL)

(73) Assignee: 270 SURGICAL LTD., Netanya (IL)

( * ) Notice: Subject to any disclaimer, the term of this patent is extended or adjusted under 35 U.S.C. 154(b) by 132 days.

This patent is subject to a terminal disclaimer.

(21) Appl. No.: 16/866,706

(22) Filed: May 5, 2020

(65) Prior Publication Data

US 2020/0260938 A1 Aug. 20, 2020

Related U.S. Application Data

(63) Continuation of application No. 15/608,683, filed on May 30, 2017, now Pat. No. 10,674,897, which is a
(Continued)

(51) Int. Cl.
*A61B 1/00* (2006.01)
*G02B 23/24* (2006.01)
(Continued)

(52) U.S. Cl.
CPC .......... *A61B 1/00183* (2013.01); *A61B 1/005* (2013.01); *A61B 1/00006* (2013.01);
(Continued)

(58) Field of Classification Search
CPC ... A61B 1/05; A61B 1/00183; A61B 1/00181; A61B 1/0676; A61B 1/0008; A61B 1/0051; A61B 1/00179; A61B 1/04
See application file for complete search history.

(56) References Cited

U.S. PATENT DOCUMENTS 6,261,226 B1  7/2001 McKenna et al.
6,277,064 B1  8/2001 Yoon
(Continued)

FOREIGN PATENT DOCUMENTS

CN  103957769  7/2014
CN  104040557  9/2014
(Continued)

OTHER PUBLICATIONS

Office Action for Japanese Patent Application No. 2017-555703 dated Jun. 30, 2020 5 Pages.
(Continued)

*Primary Examiner* — Alexandra L Newton
(74) *Attorney, Agent, or Firm* — The Roy Gross Law Firm, LLC; Roy Gross (57) ABSTRACT

The subject matter discloses a multi-sensor endoscope having a dynamic field of view comprising an elongated shaft terminating with a tip section; a maneuvering section connected to the elongated shaft; at least two sensors, wherein at least one sensor is placed behind the tip section, on the maneuvering section; and one or more illuminators located on external surface of the shaft. In some cases, the sensors include a camera. The subject matter also discloses a multi-sensor endoscopy system comprising an endoscope comprising a handle and a controller, such that the maneuvering section is controlled by the controller.

16 Claims, 5 Drawing Sheets

Related U.S. Application Data continuation of application No. PCT/IL2016/050515, filed on May 15, 2016.

(60) Provisional application No. 62/160,253, filed on May 12, 2015.

(51) Int. Cl.

| | | |
|---|---|---|
| *A61B 1/05* | (2006.01) | |
| *A61B 1/005* | (2006.01) | |
| *A61B 1/06* | (2006.01) | |
| *A61B 1/313* | (2006.01) | |
| *A61B 5/00* | (2006.01) | |
| *A61B 5/01* | (2006.01) | |
| *A61B 6/00* | (2006.01) | |
| *A61B 8/12* | (2006.01) | |
| *A61B 90/30* | (2016.01) | |

(52) U.S. Cl.
CPC ........ *A61B 1/0008* (2013.01); *A61B 1/00045* (2013.01); *A61B 1/0051* (2013.01); *A61B 1/00096* (2013.01); *A61B 1/00114* (2013.01); *A61B 1/00181* (2013.01); *A61B 1/05* (2013.01); *A61B 1/051* (2013.01); *A61B 1/0676* (2013.01); *A61B 1/3132* (2013.01); *A61B 5/0035* (2013.01); *A61B 5/0086* (2013.01); *A61B 5/015* (2013.01); *A61B 6/4057* (2013.01); *A61B 8/12* (2013.01); *G02B 23/2484* (2013.01); *A61B 1/00066* (2013.01); *A61B 2090/309* (2016.02)

(56) References Cited

U.S. PATENT DOCUMENTS

| | | |
|---|---|---|
| 6,447,444 B1 | 9/2002 | Avni et al. |
| 6,846,286 B2 | 1/2005 | Suzuki et al. |
| 8,810,638 B2 | 8/2014 | Allen et al. |
| 8,813,239 B2 | 8/2014 | Tibeica et al. |
| 8,834,358 B2 | 9/2014 | Mckinley et al. |
| 9,717,396 B2 | 8/2017 | Jungbauer et al. |
| 2002/0082475 A1 | 6/2002 | Stahl et al. |
| 2004/0172012 A1 | 9/2004 | Otsuka et al. |
| 2004/0204628 A1 | 10/2004 | Rovegno |
| 2007/0219412 A1 | 9/2007 | DiGiovanni et al. |
| 2008/0058836 A1 | 3/2008 | Moll et al. |
| 2008/0108869 A1 | 5/2008 | Sanders et al. |
| 2008/0158348 A1 | 7/2008 | Karpen et al. |
| 2008/0287736 A1 | 11/2008 | Yamazaki |
| 2009/0062604 A1 | 3/2009 | Minosawa et al. |
| 2009/0247819 A1 | 10/2009 | Wilson et al. |
| 2009/0326321 A1 | 12/2009 | Jacobsen et al. |
| 2010/0262000 A1 | 10/2010 | Wallace et al. |
| 2010/0292535 A1 | 11/2010 | Paskar |
| 2011/0018988 A1 | 1/2011 | Kazakevich et al. |
| 2011/0193938 A1 | 8/2011 | Oderwald et al. |
| 2012/0203066 A1 | 8/2012 | Okazaki et al. |
| 2013/0258081 A1 | 10/2013 | Akui et al. |
| 2014/0107418 A1 | 4/2014 | Ratnakar |
| 2014/0142377 A1 | 5/2014 | Yang et al. |
| 2014/0148643 A1 | 5/2014 | Kawano |
| 2014/0180001 A1 | 6/2014 | Von Grünberg et al. |
| 2014/0180072 A1 | 6/2014 | Davies et al. |
| 2014/0343358 A1 | 11/2014 | Hameed et al. |
| 2014/0375784 A1 | 12/2014 | Massetti |
| 2015/0062153 A1 | 3/2015 | Mihalca et al. |
| 2015/0105620 A1 | 4/2015 | Oginski et al. |
| 2015/0257784 A1 | 9/2015 | Corbin et al. |
| 2015/0342690 A1 | 12/2015 | Zubiate et al. |
| 2016/0038017 A1 | 2/2016 | Robinson et al. |
| 2016/0199072 A1 | 7/2016 | Torrie et al. |
| 2017/0071473 A1 | 3/2017 | Mueller et al. |

FOREIGN PATENT DOCUMENTS

| | | |
|---|---|---|
| EP | 2145575 | 1/2010 |
| EP | 2706932 | 3/2018 |
| JP | 06066639 | 3/1994 |
| JP | 08140976 | 8/1996 |
| JP | 09122071 | 5/1997 |
| JP | 2009251574 | 10/2009 |
| JP | 2010178766 | 8/2010 |
| JP | 2013141487 | 7/2013 |
| JP | 2014519873 | 8/2014 |
| JP | 2014524819 | 9/2014 |
| WO | 2009058350 | 5/2009 |
| WO | 2012153151 A2 | 11/2012 |
| WO | 2013091782 | 6/2013 |
| WO | 201309156 | 7/2013 |
| WO | 2014061023 | 4/2014 |
| WO | 2015133608 | 9/2015 |
| WO | 2015162140 | 10/2015 |

OTHER PUBLICATIONS

International Search Report, International Application No. PCT/IL2016/050515, dated Sep. 11, 2016.
European Search Report 16792315.0-1124/ 3294109, dated Dec. 14, 2018, 8 pages.

DYNAMIC FIELD OF VIEW ENDOSCOPE

CROSS-REFERENCE TO RELATED APPLICATION

This application is a continuation of U.S. application Ser. No. 15/608,683 filed on May 30, 2017, which is a continuation of international Application No. PCT/IL2016/050515 with an international filing date of May 15, 2016, which claims priority to U.S. Provisional Patent Application No. 62/160,253 filed May 12, 2015, the entire contents of each of which are incorporated herein by reference.

FIELD OF THE INVENTION

The present specification relates generally to a multi sensor endoscope having a dynamic field of view.

BACKGROUND OF THE INVENTION

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as laparoscopy, hysteroscopy, cystoscopy, colonoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end or at the back behind the tubular shaft. The shaft is connected to a handle, which sometimes includes an ocular for direct viewing. Viewing is usually possible via an external screen.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

In one embodiment the present invention provides a multi-sensor endoscope having a dynamic field of view comprising:
 a. an elongated shaft terminating with a tip section;
 b. at least one maneuvering section;
 c. at least two sensors, wherein at least one sensor is placed behind the tip section; and
 d. one or more illuminators.
The term "behind" is defined as an area in the endoscope located towards the person holding the endoscope. That is, in case the tip section is the first section inserted into a specific tissue, the sensors located behind the tip section will be able to enter the tissue after the tip section.

In some embodiments, said maneuvering section comprises bending, rotating and or angulating section.

In another embodiment, when the endoscope comprises more than one maneuvering section, said maneuvering sections may operate separately or simultaneously.

In some embodiments each one of said maneuvering section (such as bending, rotating or angulating section) is operated manually or electrically.

In some embodiments, at least some of said sensors are placed up to 135 degrees, or 120 degrees, or 90 degrees, or 60 degrees, or 45 degrees, or 30 degrees, or 0 degrees from the elongated shaft axis at the proximal section.

In some embodiments, said sensors are pointing at different directions to one another. For example, in a three-sensor system, two sensors may be placed in opposite directions to each other, while the third sensor may be pointing to any direction.

In some embodiments, each sensor can change its viewing direction separately by using the maneuvering (e.g., rotating or bending or angulating) mechanism.

In some embodiments, one or more of said sensors is a camera.

In another embodiment, each of said cameras comprises a Charge Coupled Device (CCD) or a Complementary Metal Oxide Semiconductor (CMOS) image sensor.

In some embodiments, said multi sensor endoscope include thermal sensor or infrared (IR) light sensor, ultra violet (UV) sensor, an ultrasound sensor or a x-ray sensor.

In another embodiment one or more of said sensors that are located behind the tip section, may be located in one or more of the sections behind the tip section.

In some embodiments, at least one of said cameras comprises a lens assembly providing a field of view of 45 degrees or more.

In some embodiments, at least one of said cameras comprises a lens assembly providing a field of view of 60 degrees or more.

In some embodiments, at least one of said cameras comprises a lens assembly providing a field of view of 80 degrees or more.

In some embodiments, at least one of said cameras comprises a lens assembly providing a field of view of 100 degrees or more.

In some embodiments, at least one of said cameras comprises a lens assembly providing a field of view of 120 degrees or more.

In some embodiments, at least one of said cameras comprises a lens assembly providing a field of view of 140 degrees or more.

In some embodiments, at least one of said cameras comprises a lens assembly providing a focal length of approximately 2-20 centimeters.

In some embodiments, at least one of said cameras comprises a lens assembly providing a focal length of approximately 2-18 centimeters.

In some embodiments, at least one of said cameras comprises a lens assembly providing a focal length of approximately 2-15 centimeters.

In some embodiments, at least one of said cameras comprises a lens assembly providing a focal length of approximately 2-13 centimeters.

In some embodiments, at least one of said cameras comprises a lens assembly providing a focal length of approximately 2-10 centimeters.

In some embodiments, fields of view of said cameras are at least partially overlapping from a specific distance and specific direction of the viewing direction camera lenses, such that an object from a the specific distance of the interest viewed via said one camera remains in the field of view of said second camera while said tip section or other section behind the tip section is being turned or fixed towards the object, and at least until the object becomes visible through one of said cameras.

In some embodiments, said sensors and said illuminators are configured to operate separately or simultaneously in various combinations.

In some embodiments, each of said illuminators comprises a light-emitting diode (LED).

In some embodiments, at least one of said illuminators is configured to emit white light.

In some embodiments, at least one of said illuminators is configured to emit ultraviolet light.

In some embodiments, at least one of said illuminators is configured to emit infrared light.

In some embodiments, at least one of said illuminators is configured to emit near-infrared light.

In some embodiments, at least one of said illuminators is configured to emit light in different wavelengths.

In some embodiments, at least one of said illuminators is an ultrasound transducer to emit ultrasound signals.

In some embodiments, at least one of said illuminators is an X-ray configured to emit different X-ray wavelengths.

In some embodiments, said endoscope is a laparoscope.

In another embodiment, the present invention provides a method of achieving a dynamic field of view in an endoscope that can alternate its field of view parameters by using at least two sensors, wherein at least one sensor can move in respect to other sensor.

In another embodiment the present invention provides a multi-sensor endoscopy system comprising: an endoscope comprising a handle; an elongated shaft terminating with a tip section; a maneuvering section; at least two sensors, wherein at least one sensor is placed behind the tip section; one or more illuminators; a controller connected to said handle of said endoscope by way of a utility cable; a display connected to said controller and configured to display signals streams received from said sensors.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION OF THE INVENTION

An aspect of embodiments related to an endoscope having an elongated shaft terminating with a tip section, a maneuvering section and two or more sensors, wherein at least one sensor is placed behind the tip section. Preferably, the sensor is a camera. For simplicity of discussion the sensors are represented by cameras, which are meant to be exemplary and illustrative, not limiting in scope.

Figure 1:
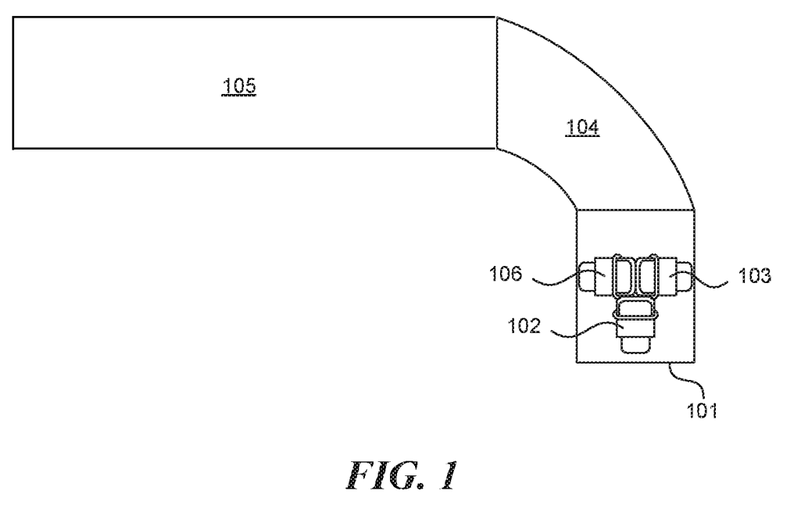
FIG. 1 shows a cross sectional view of a prior art endoscope.

Reference is now made to FIG. 1, which shows across sectional view of a prior art endoscope, in this example three cameras (102, 103 and 106) (as well as other elements such as a light source or a working channel, not shown) are located at the tip section (101). In this case when the shaft (105) is moving or bended, using bending section (104), the entire tip is moving and as a result the whole sensor's image is moving as well without the option of changing the directions of the cameras relatively to each other. The present invention provides an endoscope having one or more maneuvering section such as bending, rotating or angulating sections. In this configuration each sensor may be operated independently and as a result a dynamic field of view may be obtained.

As used herein, the term "rotating section" refers to a section of the endoscope, which can be rotated around the shaft axis for up to 360 degrees or less.

As used herein, the term "bending section" refers to a section of the endoscope which has a plurality of links, which enable the turning of a tip section and or other section placed in front of the bending section in different directions.

As used herein, the term "angulating section" refers to a section of the endoscope, which enables the turning of the tip section and or other section placed in front of the angulating section in different directions.

Figure 2A:
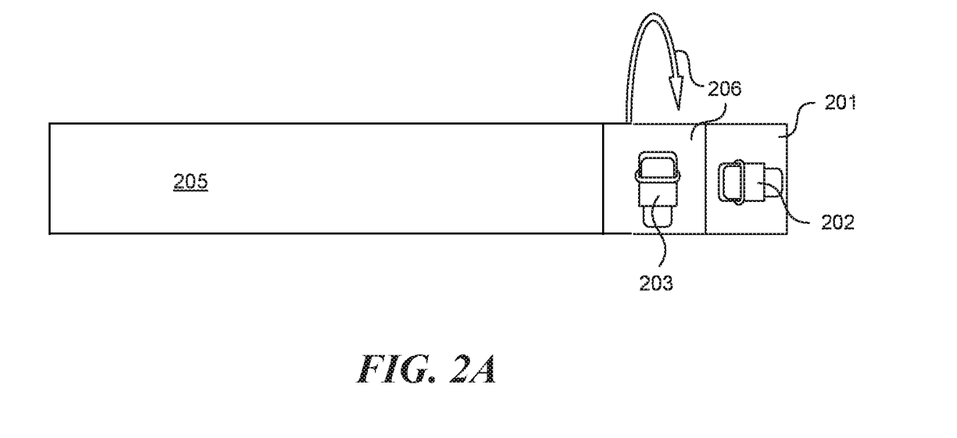
FIGS. 2A-B show cross sectional views of a multi-sensor endoscope having a rotating section, according to exemplary embodiments of the present invention.

During endoscopic procedures many times there is a need to extend the field of view to see more organs, and even the entire abdominal cavity, while another camera may still view another location. In order to achieve that, the present invention enables to change the direction of one camera relative to a direction of another camera during the operation. FIG. 2A shows an example of an endoscope, having a rotating section (206), a front pointing camera (202) located at the tip section (201) and another camera positioned at 90 degrees along the shaft axis (203) located at the rotating section 206.

Figure 2B:
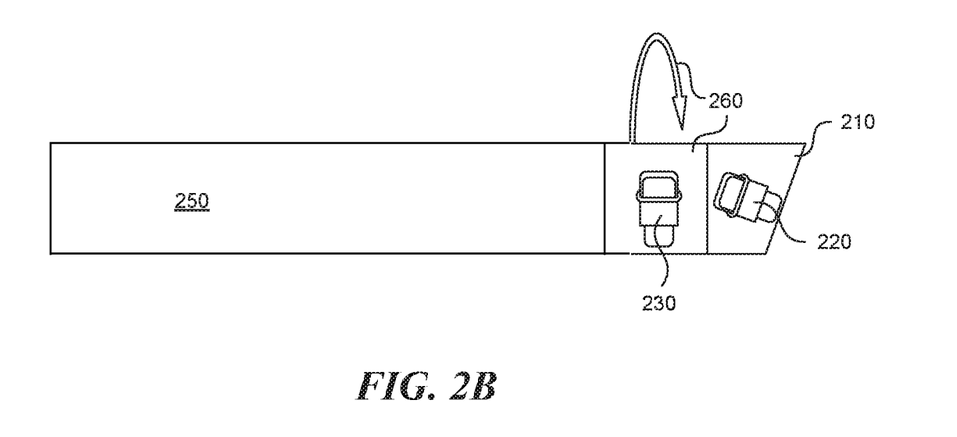

Advantageously, this configuration allows obtaining a dynamic field of view. Here, one sensor, e.g. the front pointing camera remains still, while the additional sensor, located at the rotating section 206 may be rotated separately, with no need to rotate the shaft 205. FIG. 2B shows another example of a similar endoscope having a rotating section (260), a tilted front pointing camera (220) located at the tip section (210) and another camera positioned at 90 degrees along the shaft axis (230) located at the rotating section 260. Since the front camera 220 is tilted, when only the shaft (250) is (mechanically) rotated, the whole sensor image will move. Using a rotating section as described herein enables to obtain a dynamic field of view.

Figure 3:
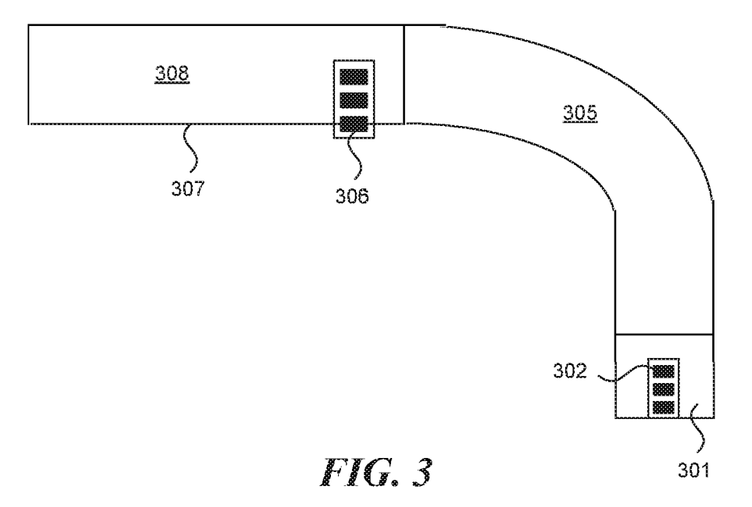
FIG. 3 shows a cross sectional view of a multi-sensor endoscope having a bending section, according to exemplary embodiments of the present invention.

Another way to obtain a dynamic field of view is by using a bending section behind the tip section. FIG. 3 shows an example of an endoscope having a bending section (305) behind the tip section (301), a front pointing camera (302)

located at the tip and a side pointing camera (306) located behind the bending section. The side pointing camera 306 is positioned on an external surface 307 of a tube 308 of the endoscope. The tube 308 comprises a hollow volume in which electronic wires carry information from the sensors to a remote system, as described in FIG. 5. This configuration allows obtaining a dynamic field of view with a wide angle of view. A similar sensor image may be obtained if an angulating section is present instead of a bending section (not shown).

Figure 4:
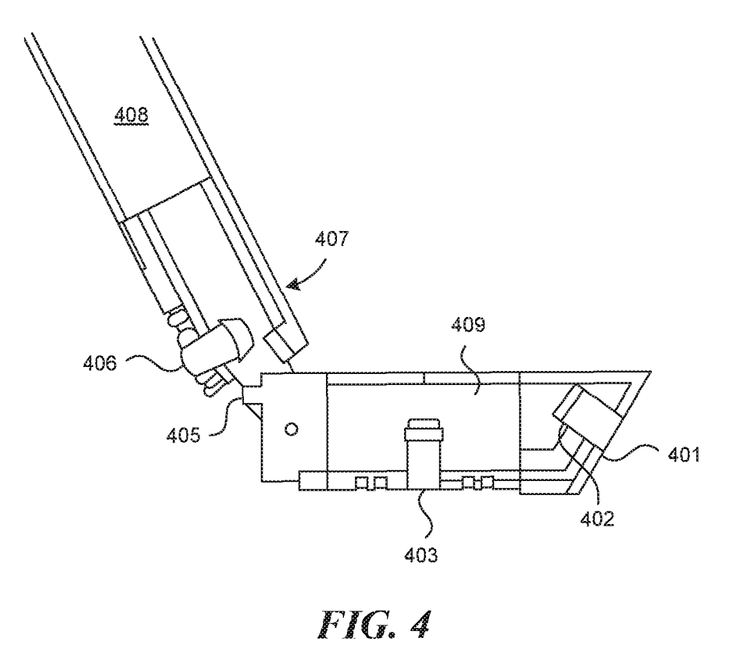
FIG. 4 shows cross-sectional view of a multi sensor endoscope having an angulating section, according to exemplary embodiments of the present invention.

However, if an angulating section is used, the control of movement is preferred. Also, when an angulating section is used instead of a rotating section, it is possible to include more sensors, e.g. cameras of the same quality, at the same proximal length. FIG. 4 shows an endoscope having an angulating section (405), a tilted front pointing camera (402) located at the frontal tip section (401), which is a portion of tip section (409). Another camera is positioned at 90 degrees along the shaft axis (403) located behind the tip section (409) and a third camera (406) located behind the angulating section (405), on an external surface 407 of the tube 408, similar to tube 308 disclosed above. This configuration allows having a dynamic field of view with a wide viewing angle.

Figure 6A:
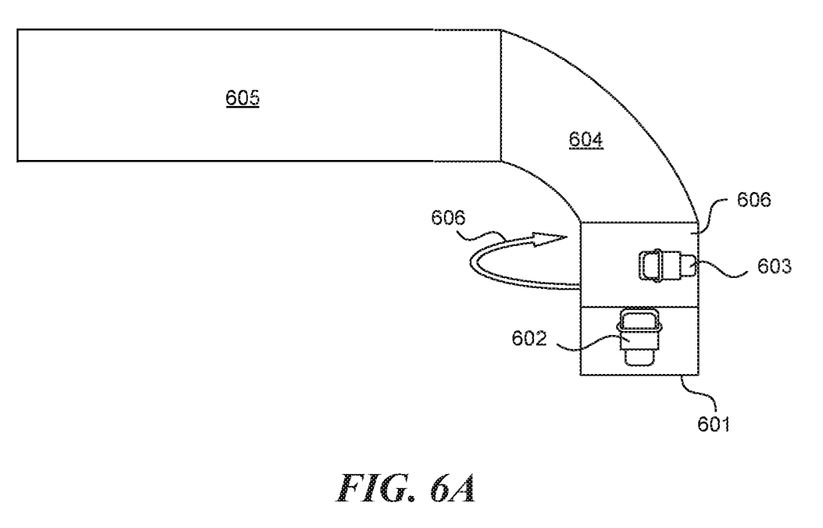
FIGS. 6A-B show cross-sectional views of a multi sensor endoscope having more than one maneuvering section, according to exemplary embodiments of the present invention.
Figure 6B:
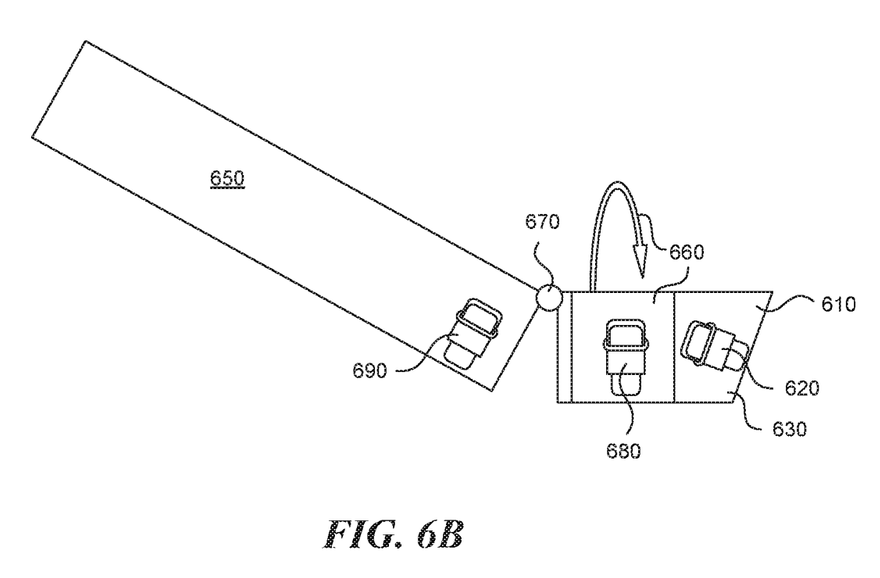

As mentioned above the multi sensor endoscope of the present invention is not limited only to one maneuvering section, but may include two or more identical or different maneuvering sections. Reference is now made to FIGS. 6A-B, in which configurations of multi sensor endoscopes having more than one maneuvering section are shown. Advantageously, in these configurations the field of view during maneuvering is highly controlled. Configuration A describes an endoscope comprising a bending section (604) and a rotating section (606), a front pointing camera (602) located at the tip section (601) and another camera at 90 degrees along the shaft axis (603) located behind the tip section may be rotated by rotating section (606). Configuration B describes an endoscope comprising an angulating section (670) and a rotating section (660), a tilted front pointing camera (620) located on an external surface 630 at the tip section (610), another camera at 90 degrees along the shaft axis (680) located behind the tip section may be rotated by rotating section (660) and a third camera at 90 degrees along the shaft axis (690) located behind the angulating section (670). Similarly, in other configurations (not shown), two or more maneuvering sections are present and two or more cameras may be positioned in each of these sections at different degrees along the shaft axis.

Figure 5:
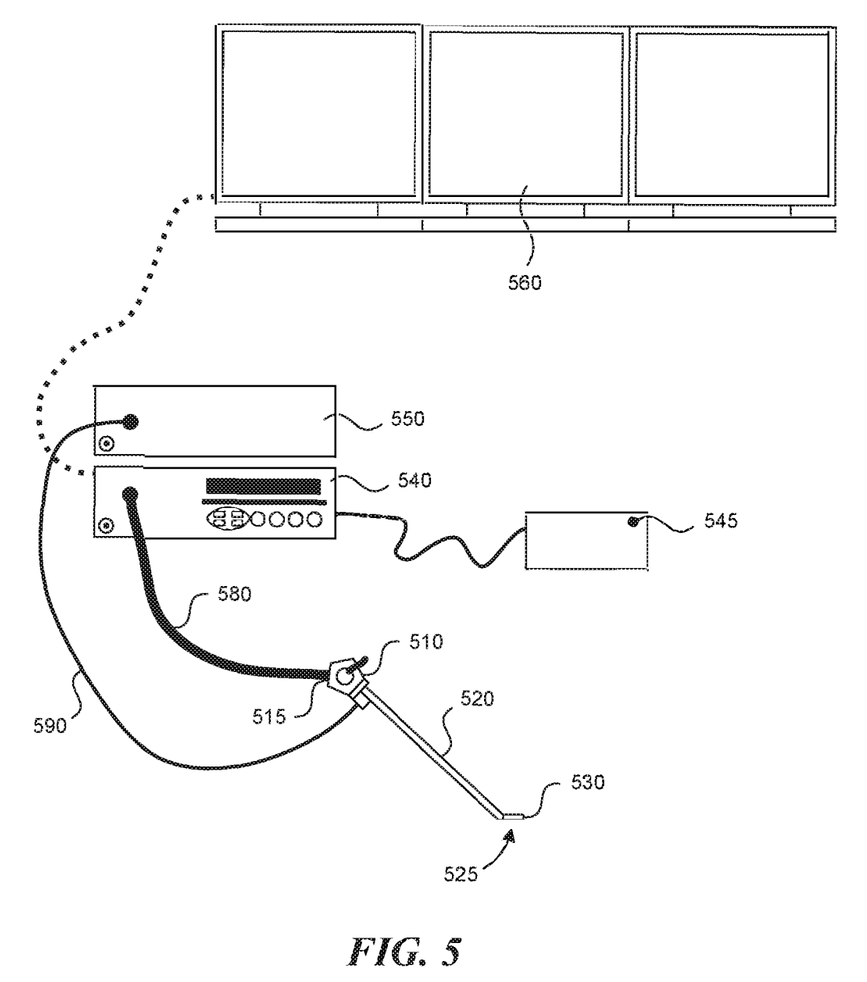
FIG. 5 shows a semi-pictorial view of a multi-sensor endoscopy system, according to exemplary embodiments of the present invention.

Reference is now made to FIG. 5, which shows a semi-pictorial view of a multi-sensor endoscopy system. The system may include a multi-sensor endoscope, such as the endoscope of FIGS. 2, 3, 4 and/or 6. The Multi-sensor endoscope may include a handle (510), from which an elongated shaft (520) emerges. Elongated shaft (520) terminates with a tip section (530). Handle (510) may be used for maneuvering elongated shaft (520) within a body cavity; the handle may include one or more knobs (515) and/or switches which control bending, rotating and or angulating sections (525). A utility cable (580) may connect between handle (510) and a controller (540). Utility cable (580) may include therein one or more electrical channels. The electrical channel(s) may include at least one data cable for receiving signals, e.g., video signals, from the front and side-pointing sensors, e.g. cameras as well. In addition the light source cable (590) may connect between the handle and (550) light source unit.

Controller (540) may govern power transmission to the endoscope's tip section (530), such as for the tip section's sensors. Controller (540) may further control the maneuvering by signals from the handle of one or more bending, rotating or angulating sections. One or more input devices, such as a keyboard (545), may be connected to controller (540) for the purpose of human interaction with the controller 540. A display (560) may be connected to controller (540), and configured to display signals such as images and/or video streams received from the sensors, e.g. cameras of the multi-sensor endoscope. Display (560) may further be operative to display a user interface for allowing a human operator to set various features of system.

Optionally, when the sensors are cameras, the video streams received from the different cameras of multi-sensor endoscope may be displayed separately on display (560), either side-by-side or interchangeably (namely, the operator may switch between views from the different cameras manually).

Alternatively, these video streams may be processed by controller (540) to combine them into a single, panoramic video frame, based on an overlap between fields of view of the cameras. In another configuration (not shown), two or more displays may be connected to controller (540), each for displaying a video stream from a different camera of the multi-sensor endoscope.

The invention claimed is:

1. A multi-sensor endoscope having a dynamic field of view, comprising:
   a. an elongated shaft;
   b. a tip section;
   c. an angulating section positioned between the elongated shaft and said tip section;
   d. a rotating section; and
   e. at least three cameras,
   wherein the angulating section is configured to tilt the rotating section and the tip section relative to longitudinal axis of the elongated shaft;
   wherein the rotating section is configured to turn the rotating section and the tip section around the longitudinal axis of the elongated shaft;
   wherein the at least three cameras comprise:
      i. a first front-pointing camera located on the tip section;
      ii. a second camera positioned on the rotating section essentially perpendicularly to a longitudinal axis of the rotating section;
      iii. a third camera located on the elongated shaft essentially perpendicularly to the longitudinal axis of the elongated shaft; and
   wherein the fields of views of the at least three cameras are at least partially overlapping during maneuvering of the angulating section.

2. The multi-sensor endoscope according to claim 1, wherein each of said at least three cameras comprises a Charge Coupled Device (CCD) or a Complementary Metal Oxide Semiconductor (CMOS) image sensor.

3. The multi-sensor endoscope according to claim 1, wherein one or more of said at least three cameras comprises a thermal sensor, an infrared (IR) light sensor, an ultraviolet (UV) sensor.

4. The multi-sensor endoscope according to claim 1, wherein the angulating section is configured to be operated separately or simultaneously relative to the elongated shaft.

5. The multi-sensor endoscope according to claim 1, wherein the angulating section is operated manually or electrically.

6. The multi-sensor endoscope according to claim 1, wherein the rotating section is operated manually or electrically.

7. The multi-sensor endoscope according to claim 1, wherein the at least three cameras are configured to be maneuvered independently.

8. The multi-sensor endoscope according to claim 1, wherein said endoscope is a laparoscope.

9. The multi-sensor endoscope according to claim 1, further comprising one or more illuminators configured to provide illumination to the first, second and/or third cameras.

10. The multi-sensor endoscope according to claim 9, wherein each of said one or more illuminators comprises a light-emitting diode (LED).

11. The multi-sensor endoscope according to claim 9, wherein the first, second and/or third cameras are positioned on external surfaces of the tip section, the rotating section and the elongated shaft, respectively.

12. The multi-sensor endoscope according to claim 1, wherein at least one of said cameras comprises a lens assembly providing a field of view of 140 degrees or more.

13. The multi-sensor endoscope according to claim 1, wherein said cameras comprises a lens assembly providing a focal length of approximately 2-20 centimeters.

14. The multi-sensor endoscope according to claim 1, wherein the field of view of first, second and/or third cameras is at least partially overlapping from a specific distance and a specific direction of each camera of said at least two cameras, such that an object viewed at the specific distance via one camera remains in the field of view of another camera during tilting and/or rotation, and at least until the object becomes visible through the other camera.

15. The multi-sensor endoscope according to claim 1, wherein one or more of the at least three cameras have a lens assembly providing a field of view of 100 degrees or more.

16. The multi-sensor endoscope of claim 1, wherein the front pointing camera is tilted relative to a longitudinal axis of the tip section.

\* \* \* \* \*